United States Patent [19]
Sackner et al.

[11] Patent Number: 6,047,203
[45] Date of Patent: Apr. 4, 2000

[54] PHYSIOLOGIC SIGNS FEEDBACK SYSTEM

[75] Inventors: Marvin A. Sackner, Miami Beach; D. Michael Inman, Miami, both of Fla.

[73] Assignee: Nims, Inc., Miami Beach, Fla.

[21] Appl. No.: 09/040,536

[22] Filed: Mar. 17, 1998

Related U.S. Application Data

[60] Provisional application No. 60/039,330, Mar. 17, 1997.

[51] Int. Cl.$^7$ .................................. A61B 5/04; A61B 5/02
[52] U.S. Cl. .......................... 600/388; 600/301; 600/386; 600/389; 600/481; 600/483; 600/508; 600/509
[58] Field of Search ...................................... 600/483, 300, 600/301, 386, 388, 389, 390, 481, 508, 509

[56] References Cited

U.S. PATENT DOCUMENTS

| | | | |
|---|---|---|---|
| 4,016,868 | 4/1977 | Allison | 600/388 |
| 4,572,197 | 2/1986 | Moore et al. | 600/504 |
| 4,981,139 | 1/1991 | Pfohl | 600/484 |
| 5,007,427 | 4/1991 | Suzuki et al. | 600/436 |
| 5,348,008 | 9/1994 | Bornn et al. | 600/386 |
| 5,353,793 | 10/1994 | Bornn | 600/301 |
| 5,611,085 | 3/1997 | Rasmussen | 2/102 |
| 5,820,567 | 10/1998 | Mackie | 600/519 |

*Primary Examiner*—Max Hindenburg
*Assistant Examiner*—Navin Natnithithadha
*Attorney, Agent, or Firm*—Cohen, Pontani, Lieberman & Pavane

[57] ABSTRACT

A non-invasive physiologic signs monitoring device includes a garment with electrocardiogram electrodes and various inductive plethysmographic sensors sewn, embroidered, embedded, or otherwise attached to the garment with an adhesive. The garment is in the form of a shirt. When the garment is fitted over the torso of the patient to be monitored, the electrodes and sensors generate signals in response to the physiologic signs of the patient. The signals are transmitted to a recording/alarm device where they are monitored for adverse conditions and logged. When an adverse condition or other preprogrammed condition occurs, a message is communicated to the patient by either an audio message or a display. The recording/alarm unit is also connectable to a remote receiving unit for monitoring by a health care professional or other machine.

42 Claims, 3 Drawing Sheets

3
PHYSIOLOGIC SIGNS FEEDBACK SYSTEM

This application claims benefit of Provisional Appl. 60/039,330 filed Mar. 17, 1997.

BACKGROUND OF THE INVENTION

1. Field of the Invention

The present invention relates to a non-invasive physiologic monitoring system which includes a garment incorporating an array of sensors and communications for transmitting monitored physiological signals to a recording/alarming unit.

2. Description of the Related Art

The administration of health care has been shifting from traditional hospital-based care to home-based self care due to an increase in medical literacy and the complex medical technology that is being introduced to the home and skilled nursing facility environments. This trend requires skilled nursing facilities or at-home utilization of devices for monitoring physiologic signs of a patient as an objective measure of health status. Furthermore, such at-home devices must provide the same results as would be obtained in a hospital by nurses and other professional health care providers. Non-invasive monitors are preferred for use outside of the hospital because of their lack of risk of negative effects associated with invasive sensors that must be placed within the body, such as intravascular catheters.

Systems for measuring a patient's "vital signs" have been described by others. For example, U.S. Pat. No. 4,981,139 discloses a vital signs monitoring and communication system. This system, however is used for monitoring a patient under anesthesia. Furthermore, it uses invasive sensors, such as an esophageal stethoscope, that are cabled to a nearby receiver. Messages from the receiver are then transmitted by an infrared link to the health care provider. The system messages merely identify which of the monitored physiologic signs, such for example is 'heart' or 'temperature', is in an alarm condition when such an alarm condition occurs.

Other prior art systems include monitoring devices that respond to short term events, such as breathing monitors which monitor for apneas and brief episodes of tachycardia. Therefore, there still exists a need for a non-invasive physiologic signs monitor that can be used in a home setting so as to allow patients who would otherwise be required to stay at a hospital to live at home while maintaining the monitoring necessary for their particular health conditions without sacrificing the level of reliability and scrutiny that they would receive in the hospital.

SUMMARY OF THE INVENTION

The non-invasive monitor according to the present invention comprises an easily worn garment incorporating an array of sensors and wireless communications and that transmits data to a nearby recording/alarm unit. To provide an effective non-invasive monitoring system, the garment of the present invention includes a sensor array targeted to the information to be sought. The sensor array and associated circuitry on the garment are easily applied and are transparent to the user such that the garment, sensors, and associated circuitry do not restrict the personal activities of the patient being monitored. The recording/alarm unit, which receives information from the sensor array, provides easily understood indications that the equipment is operating properly, includes an alarm for adverse or preprogrammed events, and delivers status reports to the monitored patient and/or to the health care provider in plainspoken text messages. The status reports may be delivered periodically and/or upon request. The unit recording/alarm unit may also communicate with a remote station supervised by physicians or other health care providers. The unit additionally also includes a database for the monitored information and which may be used to record information received from visiting health care providers so as to facilitate the billing of services, preparation of regulatory reports, and assessment of quality of care.

The garment incorporates inductive plethysmographic and electrocardiographic sensors with associated amplifiers and communications modules. An oscillator-demodulator unit for the inductive plethysmographic sensors within the garment has multiplex capabilities or may be implemented as separate modules tuned to different frequencies for eliminating cross-talk among the different sensors. The electrodes for the electrocardiographic sensors preferably comprise patches of graphite fiber conductive material that are sewn to the garment or otherwise fixed within the garment with an adhesive material or the like. The garment and sensors, which are designated herein as a non-invasive monitoring shirt (NimShirt), transmits data from the sensor and associated electronics to the recording/alarm unit via a wireless pathway. The recording/alarm unit is preferably relatively near the patient being monitored, such for example as within a 300 foot radius around the patient being monitored. The NimShirt transmits data at a rate ranging from approximately 25–200 points/second. Optionally, a one minute trend numerical value reduced from data processed waveforms is transmitted every five to ten minutes in which case the NimShirt may transmit data at the rate ranging from approximately 25–200 points/second only when an adverse or preprogrammed event occurs to thereby conserve the batteries powering the electronics on the NimShirt.

The recording/alarm unit responds to the transmitted data from the NimShirt with plainspoken statements through an audio system, under the control of a microprocessor. The plainspoken statements include information and recommendations for appropriate action directed to the patient being monitored and/or to his or her health provider. Multiple sensor monitors provide a great deal of interrelated, relevant information but may also provide redundant and irrelevant information. Therefore, the microprocessor of the invention is programmed with verbal phrases based upon on-off logic and/or expert systems that execute decisions based on the significance of each portion of data collected. The recording/alarm unit of the present invention monitors the sensor signals for short-term adverse events and also delivers plainspoken statements based on analysis of trends collected over several minutes or hours of data. The recording/alarm unit may also transmit this information to an attending physician or health care provider for review and modifications of these statements at a central site; such transmission may be via the internet, cable, or telephone connections, or by way of a wireless link. The data from the sensors may be logged in a database for tracking the data and sensed conditions of patients and for comparison to other patients. The results of the tracking and comparison may result in changes in the diagnostic algorithms and action recommendations. The system may receive demographic, historical, physical diagnostic information, and responses to treatments from visiting health care providers through a PC, notebook, or handheld computer. The system may also be used to monitor medication compliance. Although the inventive system is primarily intended for use at home and in skilled nursing facilities, the current trend toward reducing staff in hospitals and other sites for the delivery of health care makes this system useful in those facilities as well. Finally, the system of the present invention may be employed for monitoring populations exposed to hazardous materials.

Table 3 shows a comparison of functional attributes of the sensors of the inventive NimShirt to conventional technology.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims.

BRIEF DESCRIPTION OF THE DRAWINGS

In the drawings, wherein like reference characters denote similar elements throughout the several views.

DETAILED DESCRIPTION OF THE PRESENTLY PREFERRED EMBODIMENTS

Figure 1:
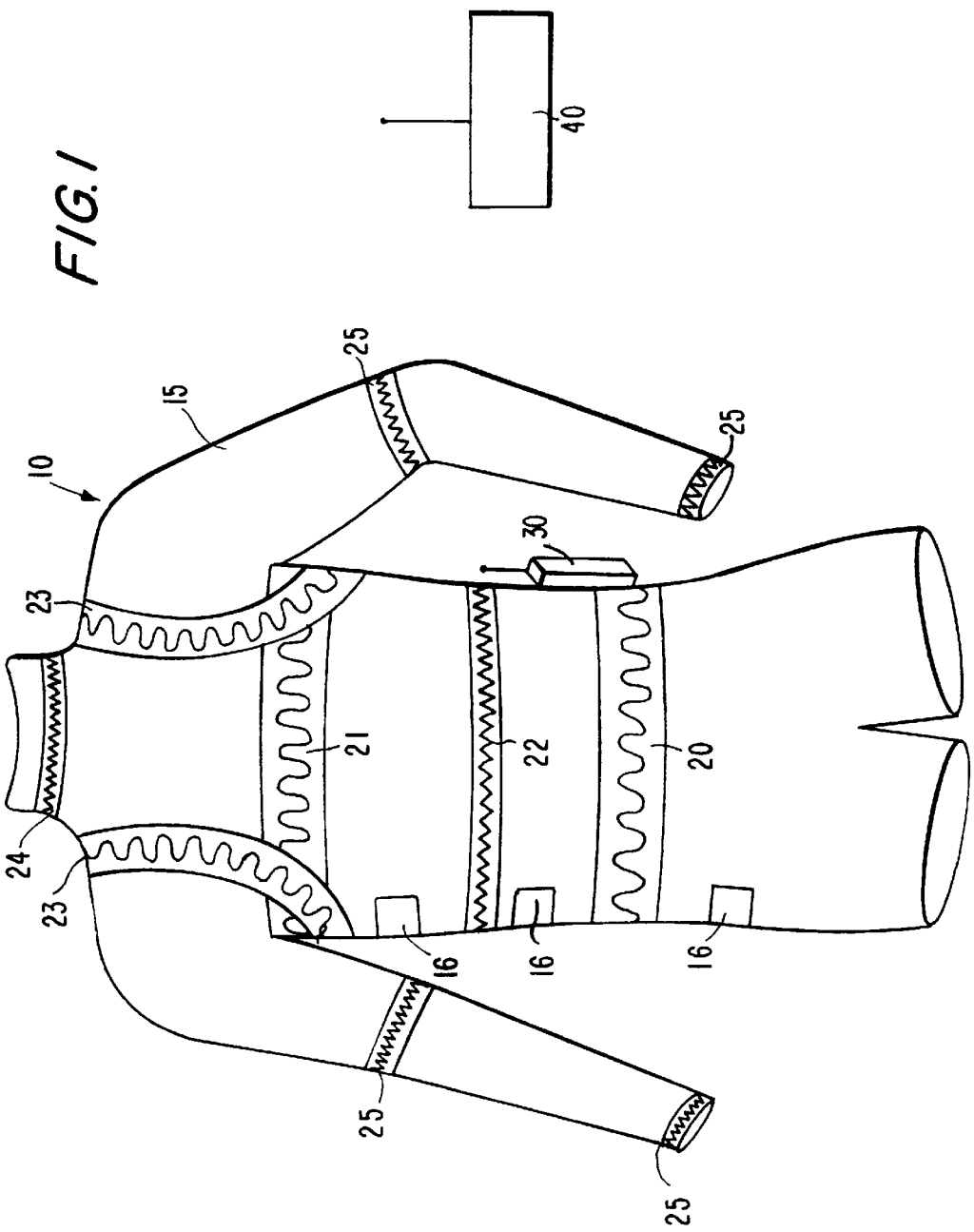
FIG. 1 is a front view, partly in section, of a NimShirt constructed in accordance with to the present invention.
Figure 2:
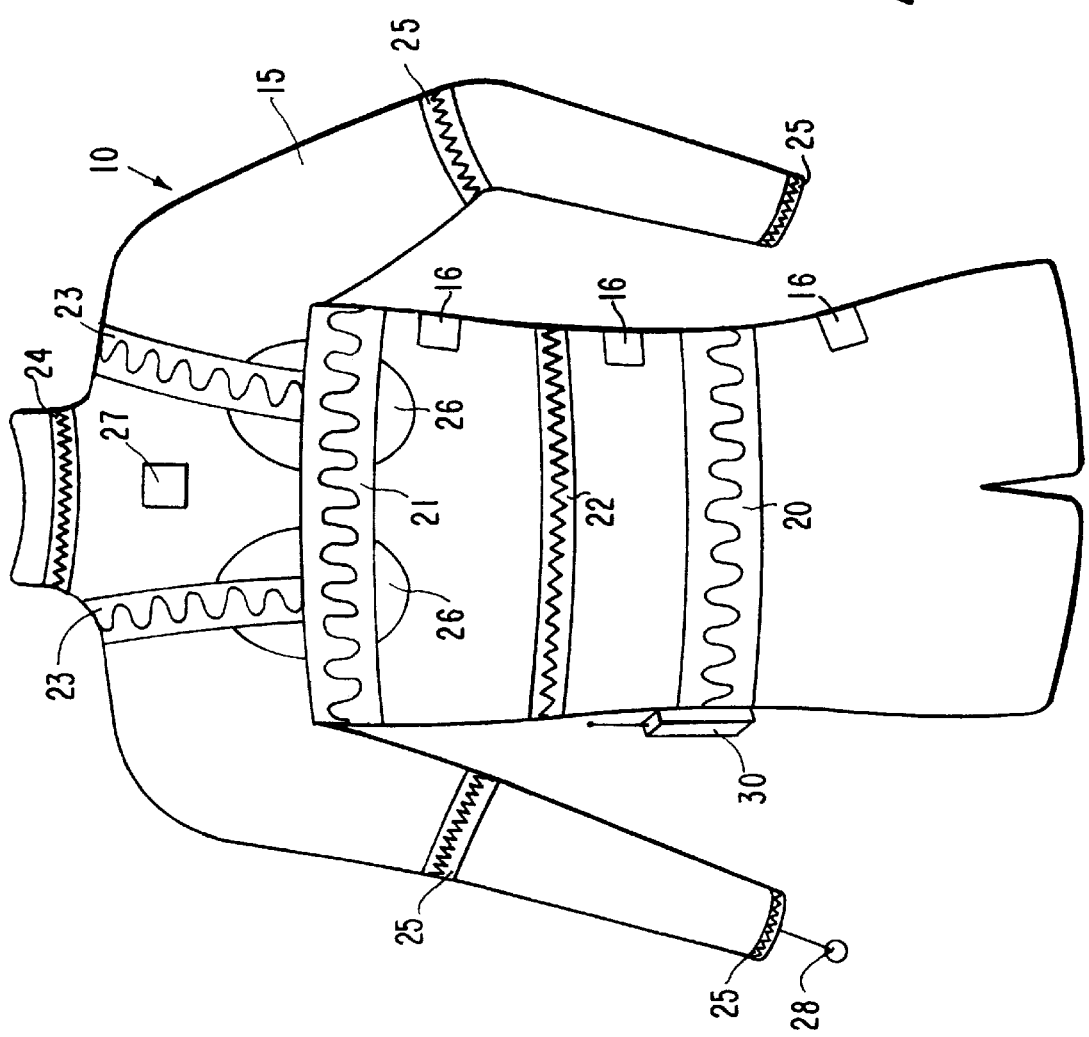
FIG. 2 is a rear view, partly in section, of the NimShirt of FIG. 1.

Referring to FIGS. 1 and 2, a preferred embodiment of the inventive non-invasive physiologic monitoring shirt (NimShirt) 10 comprises electrically conductive plethysmographic sensors 20–25 which are embroidered, sewn, embedded, woven, printed onto or otherwise affixed to or carried on a turtle-neck, long sleeved garment 15 that is worn over and about the torso of a patient (not shown) to be monitored. The sensor 20–25 comprises an integral part of the garment 15 via their attachment to the garment 15. The NimShirt 10 further includes electrocardiographic electrode sensors 26 that are sewn, embedded, or fixed with adhesive or the like to the inside of the rear face of the garment 15. The garment 15 is fastened snugly onto the body using fastening devices 16 such, for example, as velcro strips or ties.

Figure 3:
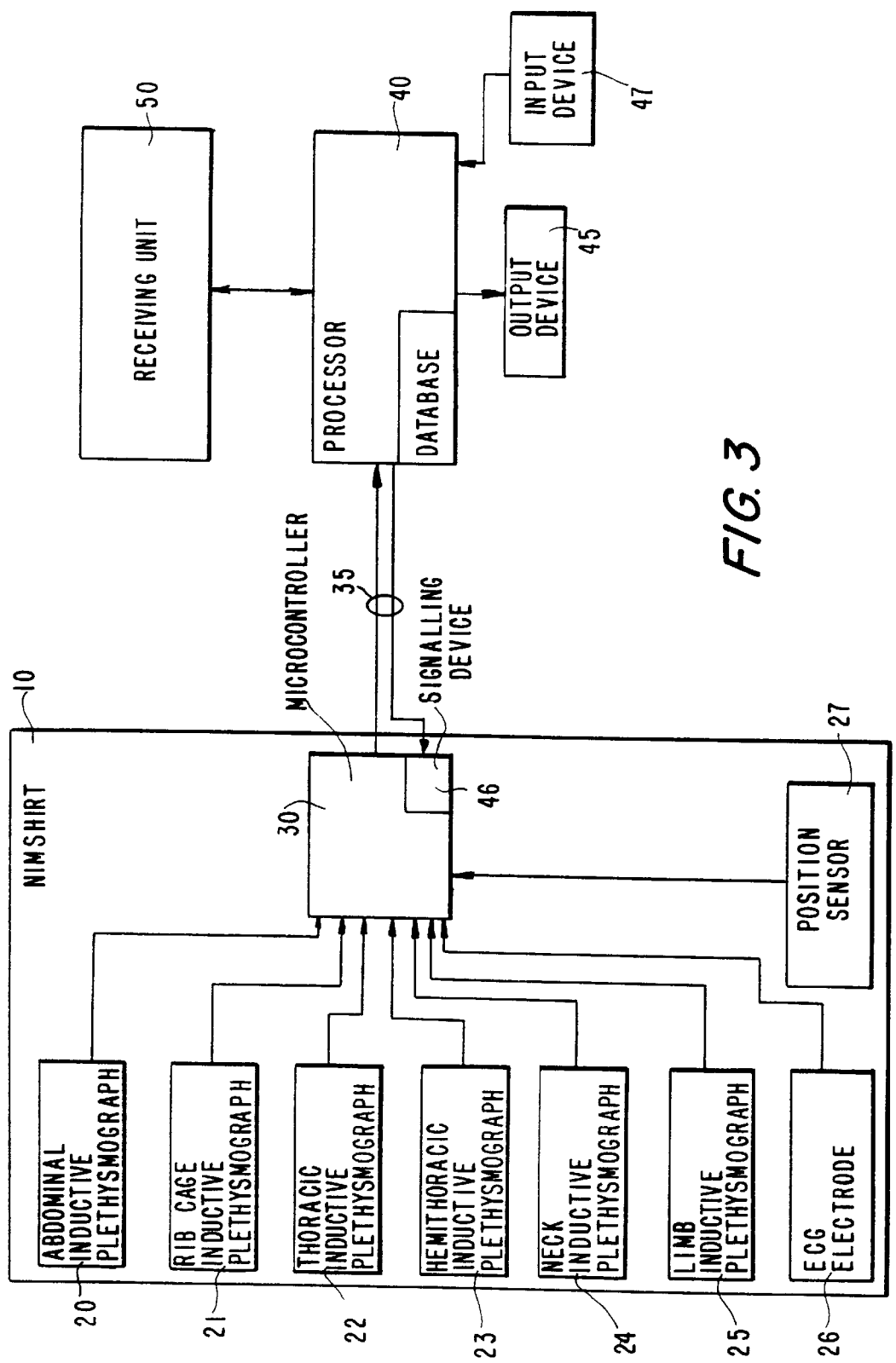
FIG. 3 is a block diagram of the non-invasive monitoring system of the present invention.

Each of the sensors 20–26 are connected to a microcontroller unit 30 that is attached to or carried on the garment 15. Microcontroller 30 comprises an oscillator-demodulator unit for the inductive plethysmographic sensors 20–25 and either has multiplex capabilities or takes the form of a plurality of separate oscillator modules tuned to respectively different frequencies for eliminating cross-talk between the various sensors 20–25. The microcontroller unit 30 is shown attached to a side of the garment 15 at the waist of the patient to be monitored; it may, however, alternately be attached or carried in any comfortable position or location on or about the body of the patient. As seen in FIG. 3, the microcontroller collects the monitored signals from the sensors 20–26 and transmits them via a wireless communication link 35 to a remote recording/alarm unit 40 which includes a processor for determining alarm conditions and providing datalogging functions. The recording/alarm unit 40 incorporates an output device 45 such, for example, as a sound system, for providing alarms and action recommendations to the patient and/or healthcare provider in a preferably nearby area. The sound system in a preferred form provides these alarms and action recommendations as plainspoken audible statements.

Instead of or in addition to a sound system that reproduces audible messages, the output device 45 may be a display unit such as a monitor screen that displays the messages as contrasted with reproducing them audibly. This alternative may for example be used when the patient to be monitored is deaf or hard of hearing, or where the message contains a great deal of information which may be difficult to comprehend or appreciate when merely listening to an audible message. Such a modification also requires an additional signal to be directed to the patient being monitored when a new message is present, since the patient may not be within a line of sight of the recording/alarm unit 40. For this purpose, microcontroller 30 may include or activate a signalling device 46, such as a illuminitable lamp for informing the patient being monitored that there is a new message at the recording/alarm unit 40. Since microcontroller 30 is mounted on the NimShirt 10, the signalling device may also when activated effect a vibration of the microcontroller 30 which will be felt by the patient being monitored. The signalling device 46 may also be located at the recording/alarm device 40 in some embodiments, as for example where the signalling device 46 produces a sound or illuminates a lamp.

The recording/alarm unit 40 may also be connected or linked to a receiving unit 50 located at a separate or remote site that is attended by health care providers for transmitting the data received from the NimShirt 10, and associated alarms and/or messages, to receiving unit 50 so that the health care providers at the remote site may view and analyze the data. The transmission to the remote site may be made via a modem, internet connection, satellite hookup, cable, or any other communication system or arrangement. The connection between recording/alarm unit 40 and receiving unit 50 may also allow health care providers at the remote site to return information to the unit 40. For example, the health care providers may wish to provide specific instructions to the patient being monitored. In addition, the recording/alarm unit 40 may log the data received from the NimShirt 10 to a database for tracking the condition of the patient and for comparison to other patients. This enables continued modification and refinement of the diagnostic algorithm in the recording/alarm unit 40 and action recommendations.

With continued reference to FIGS. 1 and 2, the structure and operative functionality of the individual sensors 20–26 will now be explained in further detail. A neck inductive plethysmographic sensor 24 is sewn, embroidered, or embedded, for example, to the turtleneck area of the garment 15. Sensor 24 monitors jugular venous pulse, carotid arterial pulse, intrapleural pressure swings related to respiration, contraction of neck muscles, and swallowing deflections. Estimations of the central venous pressure from the data collected by sensor 24 compare well to values simultaneous recorded using intravascular catheters. Since the jugular venous pulse depicts an 'a' wave related to arterial contraction, which is a substitute for the 'P' wave of the electrocardiogram, data from sensor 24 may aid in differentiating arrythmias and supraventricular tachycardia with aberrant ventricular conduction from ventricular tachycardia. The recording of the arterial pulse in conjunction with an electrocardiograph allows computation of the systolic time intervals which may be used for estimating the mechanical function of the left ventricle. Sensor 24 may also record swallowing deflections as sharp, transient waveforms superimposed upon slower respiratory deflections and vascular pulses.

An abdominal plethysmographic sensor 20 and a rib cage plethysmographic sensor 21 are sewn, embroidered, or embedded, for example, in the abdominal and rib cage portions of the garment 15 for monitoring the expansion and contraction of the abdomen and rib cage, respectively. The sensors 20 and 21, used together, are referred to as a respiratory inductive plethysmograph and are employed for recording breathing patterns.

A thoracic inductive plethysmograph sensor 22 is sewn, embroidered, or embedded, for example, into the garment 15 around the xiphoid process region. Sensor 22 may be formed of one or more plethysmographic coil-type sensors and operatively monitors the beat by beat ventricular volume during breath holding and during slow breathing. Analysis of the resulting waveforms by the microcontroller recording/alarm unit 40 enables computation of changes in cardiac output and stroke volume and of parameters related to systolic and diastolic functions. Analysis of a derivative of the ventricular waveforms yields parameters analogous to Echo-Doppler measurements of the mitral valve. The deceleration time of the mitral flow velocity parameter can provide an estimate of pulmonary capillary wedge pressure in patients with compromised left ventricular function. Longer deceleration times are consistent with normal and shorter times with elevated pulmonary capillary wedge pressures.

Two hemithoracic inductive plethysmographic sensors 23 are sewn, embroidered, or embedded, for example, into the garment 15 on the right and left sides of the upper thorax. These sensors 23 enable measurement of inequalities in regional expansion with breathing and paradoxical motion between the two hemithoraces. Such inequalities suggest pleural effusion, diaphragmatic hemiparesis, or pneumothorax and may aid in diagnosis of certain clinical circumstances.

Limb inductive plethysmographic sensors 25 are sewn, embroidered, or embedded, for example, at the elbow and wrist areas of the garment 15. These sensors 25 record vascular pulses over the vessels of the limb or extremity about which it is placed. The sensors 25 may be used to record peripheral blood flow using standard plethysmographic occlusion techniques, pulse transit time by using a pair of separated sensors 25 on the extremity, or pulse transit time from arterial pulse in the neck (via neck inductive plethysmography) to the extremity (via limb inductive plethysmography). Pulse transit times offer a means for continuous recording of systolic blood pressure. The sensors 25 may serve as a sensor to provide wideband external pulse recording of systematic blood pressure during external cuff deflation.

The preferred embodiment of the NimShirt 10 further includes electrocardiogram (ECG) electrode sensors 26 (FIG. 2). The ECG electrode sensors 26 may each by way of example comprise a large patch of graphite electrically conductive fiber material affixed to the inside of the back or rear wall or panel of the garment 15 with a flexible adhesive material. The ECG electrode sensors 26 may alternatively comprise, by way of additional example, a mixture of electrically conductive graphite and silicone gel that is painted onto the inside wall of the garment 15. The sensors 26 contact the skin directly without the need for electrically conductive gel between the electrodes and the surface of the skin. Although the ECG electrode sensors 26 are shown in FIG. 2 as mounted on the upper portion of the rear panel of the garment 15, they may alternately be mounted at any location about the garment at which an ECG signal may be detected on the patient's body.

The combination of RR intervals of the ECG measurements from sensors 26 and the tidal breath waveform from the respiratory inductive plethysmographic sensors 20, 21 as described above may be used to determine respiratory sinus arrhythmia which is a measure of autonomic nervous system function. High values of this measure signify predominant parasympathetic nervous system activity and low predominant sympathetic nervous system activity.

A body position sensor 27 may also be sewn, embroidered, or embedded, for example, in the garment 15 to indicate the patient's posture. Body position sensor 27 may comprise one or more off-the-shelf accelerometers.

Finally, a pulse oximeter sensor 28 (FIG. 2) may also be used in conjunction with the NimShirt 10. The pulse oximeter sensor 28 is generally placed at a distal fingertip of the patient or subject to measure arterial oxygen saturation and body movements. Although the pulse oximeter 28 need not be carried on or as a direct component of the NimShirt 10, detected information from oximeter 28 may be treated in a manner similar to data from sensors 20–26 by microcontroller 30 and recording/alarm unit 40. True values of arterial oxygen saturation are thereby distinguishable from values affected by motion artifacts using appropriate software algorithms.

The recording/alarm unit 40 operatively provides, by way of illustrative example, the following functionality:

messages assuring proper functioning of the monitor, such for example, as "system operating properly";

messages concerning actions to be taken in the event of malfunction, such, for example, as "system not operating properly, make sure the disk is inserted properly", or "system malfunction, contact the equipment manufacturer" (the name and address may also be supplied), messages concerning correct or incorrect placement and detachment of sensors 20–26 and their lead wires;

messages relating to vital signs information, significance, and actions to be taken by the patient in response thereto;

periodic messages concerning the stability of vital signs at preselected intervals or upon request of the patient or health care provider for assurance purposes, such for example, as "it is now 10AM and there has been no change in the vital signs";

messages relating to specialized physiologic signs information, significance, and recommended actions in response thereto;

directions including instructions entered by an attending health care provider, and reminders directing the patient to take medications (the recording unit may log compliance by monitoring when the patient swallows if the medication is to be taken orally, or monitoring breathing patterns if the medication is to be taken is in aerosol form).

In addition to providing such messages, the recording/alarm unit 40 may monitor the patient for effectiveness and proper functioning of assisted ventilatory and continuous positive air pressure (CPAP) devices. The recording/alarm unit 40 also logs data into a database as physiologic waveforms for one-minute numerical trends which may be transmitted to the remote receiving unit 50 automatically or upon receipt of a request for review by the provider at the remote receiving unit 50.

Tables 1 and 2 provide examples of common disease related diagnoses and facility types and the adverse conditions which can be monitored by the sensors of the NimShirt 10. The tables also list the various functions of each sensor for each adverse condition to be monitored.

Instead of concurrently collecting data from all of the sensors and detectors of the NimShirt 10, the types of physiologic signs to be monitored may be limited as a function of the specific condition of the patient. For example, if a patient has asthma, pertinent signs such as respiratory drive/ventilation (peak inspiratory flow/ventilation and/or peak inspiratory acceleration/ventilation) should be monitored closely as non-invasive signs of increasing bronchospasm above a predetermined threshold. This measure will be utilized to provide directions to the monitored patient via output device 45, such for example, as "you have signs of bronchospasm; please take your aerosol medication now!" If aerosol medication is taken correctly and the proper breathholding pattern is observed by the recording/alarm unit 40, then output device may state, "aerosol taken, good!" If after 30 minutes, there is no improvement or there is a worsening of specific measures and/or vital signs, the recording/alarm unit 40 may state, "call your doctor immediately!" or "get transportation and go immediately to the emergency room."

As another specific example, if the patient has chronic heart failure, then the deceleration time from the derivative of the left ventricular volume curve obtained with the thoracocardiograph (sensor comprising inductive plethysmographic band around the thorax at a level neat the xiphoid process), the central venous pressure (sensor comprising the neck inductive plethysmograph), and respiratory sinus arrhythmia (sensors comprising respiratory inductive plethysmograph and electrocardiograph) should be closely monitored. The deceleration time from echo-doppler estimation of transmitral blood flow (equivalent to the mathematical derivative of the left ventricular waveform obtained with thoracocardiography) has been found to be the most predictive sign that hospital admission is needed for treatment of chronic heart failure. In one study, values below 125 msec were the threshold associated with required hospital admission. Thresholds may be programmed into the recording/alarm unit 40 so that instructions are delivered to the patient being monitored before the 125 msec level is reached. For example, if the baseline deceleration time of 160 msec falls to 140 msec, then recording/alarm unit 40 may state, "take an additional diuretic tablet today at 5 PM." If the deceleration time falls to 120 msec, the recording/alarm unit 40 may state, "call your physician immediately." Central venous pressure reflects fluid balance in the body; low values indicate hypovolemia as might take place with overdosing with diuretics, and high values with increasing severity of heart failure. Thus, if CVP on one day is 8 cm $H_2O$ and the following day is 4 cm $H_2O$, the recording/alarm unit 40 might state "call your doctor immediately for advice on your medications."

With regard to the monitoring of medicine taking compliance, the desired times of day for taking medications are programmed into the recording/alarm unit 40. At appropriate times, the unit may state "take one capsule of #1—or one capsule of verapamid now!" The recording/alarm unit 40 and/or microcontroller 30 may also include an input device 47 such, for example, as a bar code reader so that when the patient takes out a medication vial with a bar code, information from the bar code is passed to the optional bar code reader. Alternately, the patient may enter information on the medications using a manual input device 47 such as a keyboard or a simple array of buttons. By clicking one of the buttons, the patient being monitored manually updates the recording/alarm device to indicate compliance with the scheduled medicine. As mentioned above, when the patient takes medication, swallows may be logged from the neck inductive plethysmograph waveform, thereby suggesting compliance. After the taking of medication, the patient may pass the vial over the optical reader or activate a switch to create window timing marks in the data stream that can be analyzed and stored in the recording/alarm unit 40 and/or receiving unit 50.

The physiologic signs may also be programmed for monitoring effectiveness based upon CPAP or BiPAP ventilatory requirements. Nocturnal CPAP and BiPAP are often used for treatment of the obstructive sleep apnea syndrome, which is marked by apneas and increases in upper airway inspiratory resistance. The ratio of peak inspiratory flow to mean inspiratory flow (PIF/MIF), derived from the tidal volume waveform of the respiratory inductive plethysmograph 20, 21, provides a numerical value for the shape of the inspiratory flow curve. An unobstructed inspiratory flow contour has a sinusoidal shape and the value of this parameter, PIF/MIF, is $\pi/2=1.57$. As an inspiratory obstruction develops, the inspiratory flow waveform becomes flattened and approaches a PIF/MIF value of 1.0. Significant flattening begins with a threshold value at or below 1.3. In some instances, inspiratory obstruction is marked by a brief prominent spike near beginning inspiration that gives PIF/MIF values of approximately 1.85 or greater. Therefore, optimum CPAP should provide values ranging from 1.3 to 1.85. If PIF/MF is found to be equivalent to 1.2 for a predetermined period of time, then the recording/alarm unit may deliver a message to the patient or to the personal health care provider, with increasing decibels of sound until the problem is corrected, stating "increase CPAP 3 cm water pressure now". Other investigators have described algorithms for automatic adjustment of the level of CPAP pressure based upon indices related to the shape of the inspiratory flow curve.

Since CPAP is generally administered using a nasal mask, it is subject to leaks, particularly at the mask-skin interface. Leaks can be discerned by the recording/alarm unit 40 by comparing the tidal volumes between the values delivered from the CPAP apparatus and those received by the patient. The latter is obtained with respiratory inductive plethysmography using the sensors 20, 21. For example, if the inspiratory volume per breath from respiratory inductive plethysmography sensors 20, 21 was found to be 200 ml and the volume delivered by the CPAP device is 500 ml, then a leak in the CPAP system of 300 ml is indicated and the recording/alarm unit may state "wake up and adjust your mask, it is leaking." Mask leaks are also a problem in administering ventilatory support to patients with respiratory failure or respiratory muscle weakness. Monitoring of volumes delivered versus volumes received is effective in diagnosing such leaks.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

Thus, while there have shown and described and pointed out fundamental novel features of the invention as applied to preferred embodiments thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. It is the intention, therefore, to be limited only as indicated by the scope of the claims appended hereto.

TABLE 1*

| DRG or Facility Type | Example of Adverse Monitored Condition | ECG | Respiratory Inductive Plethysmograph | Neck Inductive Plethysmograph | Thoraco-cardiograph | Hemithoracic Inductive Plethysmograph | Limb Inductive Plethysmograph |
|---|---|---|---|---|---|---|---|
| Heart failure and shock | Worsening of heart failure: pulmonary edema | Increased heart rate, arrhythmia, decreased respiratory sinus arrhythmia (RSA) | Increased respiratory rate, increased respiratory drive, increased ratio respiratory drive/ventilation['ratio'] | Increased central venous pressure, decreased indices of myocardial contraction from STI's | Decreased cardiac output, increased pulmonary capillary wedge pressure from decreased deceleration time of derivative | Asymmetry in hemithoracic expansion in some cases caused by pleural effusion | |
| | Disturbed sleep due to periodic breathing or depression = daytime hypersomnolence or fatigue | N.D. | Sleep study: periodic breathing &/or early onset to REM sleep (depressive reaction) | N.D. | N.D. | | N.D. |
| Simple pneumonia & pleurisy | Worsening of pneumonia | Increased heart rate | Increased respiratory rate, increased respiratory drive | N.D. | N.D. | N.D. | N.D. |
| Cerebrovascular disorders | Cerebral edema | Decreased heart rate | Central &/or obstr. apneas/hypopneas | N.D. | N.D. | | Increased B.P. |
| Chronic Obstructive Pulmonary Disease | Respiratory muscle dysfunction | Increased heart rate | Rapid, shallow breathing, thoracoabdominal dyscoordination, increased respiratory drive | N.D. | N.D. | N.D. | N.D. |
| Respiratory infections & inflammation | Pneumonia | Increased heart rate | Increased respiratory rate, increased respiratory drive | N.D. | N.D. | N.D. | |
| Septicemia | Adult Respiratory Distress Syndrome (ARDS) | N.D. | Rapid shallow breathing thoracoabdominal dyscoordination | Decreased central venous pressure | Increased cardiac output, low or normal pulmonary capillary wedge pressure. | N.D. | Decreased B.P. |
| Circulatory disorders w/Acute Myocardial Infarction | Recurrence of Myocardial Infarction | Abnormal ECG complexes, decreased RSA | Increased respiratory rate, increased respiratory drive, increased ratio respiratory drive/ventilation | Increased central venous pressure, decreased indices of myocardial contraction from STI's | Decreased cardiac output, increased pulmonary capillary wedge pressure from decreased deceleration time of derivative | Asymmetry in hemithoracic expansion in some cases: pleural effusion | N.D. |
| Hip & femur procedures except major joint | Pulmonary embolism | Increased heart rate | Increased respiratory rate, increased respiratory drive | Increased central venous pressure | Decreased cardiac output, normal pulmonary capillary wedge pressure (increased deceleration time from derivative) | Asymmetry in hemithoracic expansion if massive congestive atectasis & pulmonary effusion occurs | N.D. |

*N.D. Not Diagnostic

TABLE 2*

| DRG or Facility Type | Example of Adverse Monitored Condition | ECG | Respiratory Inductive Plethysmograph | Neck Inductive Plethysmograph | Thoraco-cardiograph | Hemithoracic Inductive Plethysmograph | Limb Inductive Plethysmograph |
|---|---|---|---|---|---|---|---|
| Ventilator Support | Disconnect from respirator | Increased heart rate | Rapid shallow breathing or apnea | N.D. | N.D. | N.D. | N.D. |
| | Post extubation respiratory insufficiency | Increased heart rate | Rapid shallow breathing, thoracoabdominal dyscoordination, apnea | N.D. | N.D | N.D. | N.D. |
| Post-Surgical Care | Pulmonary embolism | Increased heart rate | Increased respiratory rate, increased respiratory drive | Increased central venous pressure | Decreased cardiac output, normal pulmonary capillary wedge pressure. (increased deceleration timne from derivative) | Asymmetry in hemithoracic expansion if massive congestive atelectasis occurs | N.D. |
| Brain Injury Care | Cerebral edema | Decreased heart rate | Centrad &/or obstr. apneas/hypopneas | N.D. | N.D. | N.D. | Increased B.P. |
| Cardiac Care | Fluid overloading | Increased heart rate, arhythmia, decreased RSA | Increased respiratory rate, increased respiratory drive | Increased central venous pressure, decreased indices of myocardial contraction from STT's | Increased pulmonary capillary wedge pressure (increased deceleration time from derivative) | Asymmetry in hemithoracic expansion in fraction of cases: pleural effusion | N.D. |
| | Fluid depletion | N.D. | N.D. | Decreased central venous pressure, | N.D. | N.D. | B.P. may be decreased |
| Respiratory Therapy | Respiratory muscle dysfunction | Increased heart rate | Rapid, shallow breathing, thoraco-abdominal dyscoord-ination, increased respiratory drive | N.D. | N.D. | N.D. | N.D. |
| | Unable to understand breathing exercises | N.D. | Biofeedback display of breath waveforms | N.D. | N.D. | N.D. | N.D. |
| | Bronchospasm | Increased heart rate | Increased ratio resp.drive/ventilation | N.D. | N.D. | N.D. | Pulsus paradoxicus |
| Pain Management | Overdosage of narcotics - respiratory depression | N.D. | Obstructive/mixed apneas & hypopneas, decreased respiratory rate | N.D. | N.D. | N.D. | N.D. |
| Chemotherapy | Fluid overloading from intravenous infusions | Increased heart rate | Increased respiratory rate, increased respiratory drive | Increased central venous pressure | Increased pulmonary capillary wedge pressure (increased deceleration time from derivative) | N.D. | N.D. |

*N.D. Not Diagnostic

TABLE 3

Comparisons of Current Commercial Technologies to NimShirt

| Features | Electrocardiogram | | Breathing Pattern | | | Central Venous Pressure | |
|---|---|---|---|---|---|---|---|
| | NimShirt ECG | Standard ECG | NimShirt RIP | Impedance Pneumogram. | NimShirt NIP | NimShirt Wide | Central Venous Catheter |
| Sensor Placement | Carbon electrodes embedded in NimShirt | Conductive gel electrodes on skin | Two Inductive plethysmograph sensors in NimShirt | Conductive gel electrodes or carbon strap on skin | Inductive plethysmographic sensor in NimShirt | Band LIP with Inflating Cuff | Catheter in internal Jugular vein |
| Preparation | None | Skin preparation | None | Skin preparation | None | Induct. plethysmographic sensor in | Skin incision |
| Component FDA 510(k) approved | Yes | Yes | Yes | Yes | In part- as respiratory effort monitor but not vascular | | Yes |
| Publications | | | >1250 | | 2 | | |
| Manufacturer* | Nims | H-P | Nims | Healthdyne | Nims | 0 Nims | Edwards Laboratory |
| Recording | Continuous | Continuous | Continuous | Continuous | Discontinuous | Discontinuous | Continuous |
| Comparison of Inductive Plethy to Others | Equivalent | | Markedly superior | | Equivalent | | |
| Cost of Others compared to Inductive | | Slightly cheaper | | Slightly cheaper | | | Much more expensive |

| Features | Ventricular Volume Curves | | | Hemithoracic Excursions | | Blood Pressure | |
|---|---|---|---|---|---|---|---|
| | NimShirt TCG | Automatic Border Edge Detector Echocardiogram | Echo-Doppler | Radio Nuclear Scan | NimShirt HIP | Fluorodensito-metry | Microphone or Pressure Sensor with Inflating Cuff |
| Sensors | Inductive plethysmographic sensor in NimShirt | Hand held sensor on chest | Hand held sensor on chest | Nuclear colliniator over chest sensors in NimShirt | Two inductive plethysmographic tubes | Fluoroscopy and two photomultiplier sleeve of NimShirt over bracheal artery | Sensor placed over brachial artery |
| Preparation | None | Skin preparation | Skin preparation | IV injection | None | Dark room | None |
| Component 510(k) | No | Yes | Yes | Yes | No | Yes | Yes |
| Publications | 5 | | | | Abstract | | 0 |
| Manufacturer* | Nims | H-P | H-P | Picker | Nims | ? | Critikon |
| Recording | Discontinuous | Discontinuous | Discontinuous limited | Discontinuous & | Continuous limited | Discontinuous & | Discontinuous |
| Comparison of Inductive Plethy to Others | Equivalent | | Not done | Not done | | | |
| Cost of Others compared to Inductive | | 50–75 times more expensive | 25–50 times more expensive | 50–75 times more expensive | | 10 times more expensive | 5 times more expensive |

*Representative manufacturer.

We claim:

1. A non-invasive physiological monitoring system for monitoring physiological signs of a patient, comprising:
   a garment comprising a shirt fitting over the torso of a patient to be monitored;
   a plurality of inductive plethysmographic sensors attached to and supported by said garment as an integral part of said garment for generating first signals in response to physiological signs of the patient when the garment is worn on the torso of the patient;
   an electrocardiogram (ECG) electrode attached to said garment for generating a second signal in response to another physiological sign of the patient when the garment is worn on the torso of the patient;
   a transmitter attached to said garment and connected to said plurality of plethysmographic sensors and said electrocardiogram electrode for transmitting the first and second signals from the garment; and
   a processor unit remote from the garment and comprising a first receiver for receiving the transmitted first and second signals, a monitoring unit for receiving the first signals and second signal from first receiver, and an output device for generating and outputting messages to the patient in response to and related to the first and second signals.

2. The system of claim 1, wherein each of said plurality of inductive plethysmographic sensors comprises one of a neck inductive plethysmographic sensor, a respiratory inductive plethysmographic sensor, a thoracic inductive plethysmographic sensor, a hemithoracic inductive plethysmographic sensors, and a limb inductive plethysmographic sensor.

3. The system of claim 1, further comprising a body position sensor signally connected to said processor for indicating a posture of the patient.

4. The system of claim 1, further comprising a pulse oximeter sensor signally connected to the processor.

5. The system of claim 1, wherein said processor unit further comprises a database for periodically logging the first and second signals.

6. The system of claim 1, wherein said output device comprises an audio system for generating voice messages in response to the first and second signals.

7. The system of claim 1, wherein said output device comprises a display unit for displaying viewable messages in response to the first and second signals.

8. The system of claim 7, further comprising a signalling device for activation to signal the patient when said processor unit generates a message to the patient.

9. The system of claim 8, wherein said signalling device comprises one of an illuminatable light mounted on one of the garment and the processor unit, an audible noise generating device mounted on one of the garment and the processor unit, and a vibrating device mounted on the garment.

10. The system of claim 1, wherein said processor unit comprises a second transmitter for transmitting from the processor unit said first and second signals via a communication link, and wherein said system further comprises a second receiver at a location remote from said processor for receiving the first and second signals transmitted by said second transmitter to thereby allow monitoring of the first and second signals by one of a person and a device at the remote location.

11. The system of claim 10, wherein said communication link comprises one of a telephone line connection, an internet connection, a satellite hookup, a cable connection, and a modem connection.

12. The system of claim 10, wherein said second receiver comprises means for transmitting a message to said processor unit for output to the patient via the output device.

13. The system of claim 1, wherein said processor unit further comprises an input device for one of inputting commands to said processor unit and confirming actions requested by said processor in messages output to the patient by the processor unit.

14. The system of claim 1, further comprising one of an oscillator demodulator with multiplexer functions and a plurality of oscillator modules carried on said garment and connected between said plural plethysmographic sensors and said transmitter.

15. The system of claim 1, wherein said garment comprises a long-sleeve, turtle-neck garment.

16. The system of claim 1, wherein said plural inductive plethysmographic sensors are attached to said garment as an integral part of said garment via an attachment consisting of one of sewing, embroidering, embedding, weaving and printing said inductive plethysmographic sensor into said garment.

17. The system of claim 16, wherein said ECG electrode is attached to said garment as an integral part of said garment via an attachment consisting of one of sewing and embedding said ECG electrode into said garment.

18. The system of claim 1, wherein said plural inductive plethysmographic sensors comprise a neck inductive plethymographic sensor operatively arranged for measuring jugular venous pulse, carotid arterial pulse, intra-pleural pressure swings related to respiration, contraction of neck muscles, and swallowing deflections of the patient.

19. The system of claim 1, wherein said plural inductive plethysmographic sensors comprise abdominal and rib cage inductive plethymographic sensors operatively arranged for measuring breathing patterns of the patient.

20. The system of claim 1, wherein said plural inductive plethysmographic sensors comprise a thoracic inductive plethymographic sensor operatively arranged for measuring beat by beat ventricular volume during breath holding and slow breathing of the patient.

21. The system of claim 1, wherein said plural inductive plethysmographic sensors comprise two hemithoracic inductive plethymographic sensors operatively arranged for measuring breathing and paradoxical motion between two hemithoraces of the patient.

22. The system of claim 1, wherein said plural inductive plethysmographic sensors comprise a limb inductive plethymographic sensor operatively arranged for measuring vascular pulses within a limb of the patient.

23. A non-invasive physiological monitoring system for monitoring physiological signs of a patient, comprising:
   a garment comprising a shirt fitting over the torso of a patient to be monitored;
   an inductive plethysmographic sensor attached to and supported by said garment as an integral part of said garment for generating signals in response to the physiological signs of the patient when the garment is worn on the torso of the patient;
   a transmitter attached to said garment and connected to said inductive plethysmographic sensor for transmitting the signals generated by said sensor;
   a processor unit remote from the garment and signally connected to said transmitter via a wireless communication link for receiving the transmitted signals generated by said sensor, and comprising a monitoring unit for receiving the transmitted signals and for detecting from the received signals adverse or preprogrammed conditions, and an output device for generating and outputting messages to the patient in response to the conditions detected by the monitoring unit.

24. The system of claim 23, wherein said inductive plethymographic sensor comprises a plurality of inductive plethysmographic sensors, and wherein said transmitter further comprises one of an oscillator demodulator with multiplexer functions and a plurality of oscillator modules connected to said plurality of inductive plethysmographic sensors.

25. The system of claim 24, wherein each of said plurality of inductive plethysmographic sensors comprises one of a neck inductive plethysmographic sensor, a respiratory inductive plethysmographic sensor, a thoracic inductive plethysmographic sensor, a hemithoracic inductive plethysmographic sensors, and a limb inductive plethysmographic sensor.

26. The system of claim 25, wherein said plurality of non-invasive sensors further comprises an electrocardiogram electrode.

27. The system of claim 26, wherein said ECG electrode is attached to said garment as an integral part of said garment via an attachment consisting of one of sewing and embedding said ECG electrode into said garment.

28. The system of claim 24, wherein said processor unit further comprises a database for logging the received signals on a periodic basis.

29. The system of claim 28, further comprising a receiving unit at a location remote from said processor unit and signally connected to said processor unit for receiving from said processing unit said generated signals and thereby allowing monitoring of said generated signals at the remote location.

30. The system of claim 28, wherein said long distance communication link comprises one of a telephone connection, a modem connection, an internet connection, a satellite hookup, and a cable connection.

31. The system of claim 29, wherein said processor unit is connected to said receiving unit via a long distance communication link.

32. The system of claim 29, wherein said receiving unit comprises means for transmitting a command to said processor unit for one of sending a message to the patient through said output device, reading the database, writing to the database, and altering a response of the processor unit to the received signals.

33. The system of claim 23, wherein said transmitter transmits the generated signals from the garment at a sampling rate of at least 25 points per second.

34. The system of claim 23, wherein said transmitter generates a trend value on a periodic basis from each of the generated signals and transmits from the garment to said processing unit only the periodic trend value.

35. The system of claim 34, wherein said transmitter transmits the generated signals at a sampling rate of at least 25 points per second when the monitoring unit detects an adverse or preprogrammed condition.

36. The system of claim 23, wherein said garment comprises a long-sleeve, turtle-neck garment.

37. The system of claim 23, wherein said inductive plethysmographic sensor is attached to said garment as an integral part of said garment via an attachment consisting of one of sewing, embroidering, embedding, weaving, and printing said inductive plethysmographic sensor into said garment.

38. The system of claim 23, wherein said plural inductive plethysmographic sensors comprise a neck inductive plethymographic sensor operatively arranged for measuring jugular venous pulse, carotid arterial pulse, intra-pleural pressure swings related to respiration, contraction of neck muscles, and swallowing deflections of the patient.

39. The system of claim 23, wherein said plural inductive plethysmographic sensors comprise abdominal and rib cage inductive plethymographic sensors operatively arranged for measuring breathing patterns of the patient.

40. The system of claim 23, wherein said plural inductive plethysmographic sensors comprise a thoracic inductive plethymographic sensor operatively arranged for measuring beat by beat ventricular volume during breath holding and slow breathing of the patient.

41. The system of claim 23, wherein said plural inductive plethysmographic sensors comprise two hemithoracic inductive plethymographic sensors operatively arranged for measuring breathing and paradoxical motion between two hemithoraces of the patient.

42. The system of claim 23, wherein said plural inductive plethysmographic sensors comprise a limb inductive plethymographic sensor operatively arranged for measuring vascular pulses within a limb of the patient.

* * * * *